United States Patent [19]
Bernhardt et al.

[11] Patent Number: 6,147,239
[45] Date of Patent: Nov. 14, 2000

[54] PROCESS FOR PREPARING N, N'-DISUBSTITUTED P-QUINONEDIIMINES, THEIR USE AND ORGANOSILANES CONTAINING METHACRYLOXY OR ACRYLOXY GROUPS, PROCESSES FOR THEIR STABILIZATION AND THEIR PREPARATION

[75] Inventors: Guenther Bernhardt, St. Augustin; Klaus-Dieter Steffen, Hennef; Margret Haas, Koenigswinter; Heinz Kragl, Troisdorf, all of Germany

[73] Assignee: Huels Aktiengesellschaft, Marl, Germany

[21] Appl. No.: 09/153,085

[22] Filed: Sep. 15, 1998

Related U.S. Application Data

[62] Division of application No. 08/543,932, Oct. 17, 1995, Pat. No. 5,856,542.

[30] Foreign Application Priority Data

Oct. 21, 1994 [DE] Germany .............................. 44 37 667

[51] Int. Cl.$^7$ ...................................................... C07F 7/08
[52] U.S. Cl. ............................................ 556/401; 552/301
[58] Field of Search .............................. 552/301; 556/401

[56] References Cited

U.S. PATENT DOCUMENTS

| | | | |
|---|---|---|---|
| 2,118,826 | 5/1938 | Semon et al. . | |
| 2,118,827 | 5/1938 | Semon | 552/301 |
| 2,741,625 | 4/1956 | Pedersen | 552/301 |
| 3,078,283 | 2/1963 | Hay | 552/301 |
| 3,637,769 | 1/1972 | Susi | 552/301 |
| 4,246,181 | 1/1981 | Kalopissis et al. | 552/301 |
| 4,722,807 | 2/1988 | Iwahara et al. . | |
| 4,927,948 | 5/1990 | Bernhardt et al. . | |
| 4,946,977 | 8/1990 | Bernhardt et al. . | |

FOREIGN PATENT DOCUMENTS

3832621C1  9/1989  Germany .

OTHER PUBLICATIONS

Ludovit Kotulak, et al, "The Effect of 1,4–Phenylenediamine Anitdegradants on the Photo–Oxidation of Selected Liquid Hyrdrocarbons", Collection Czechoslovak Chem. Comm., vol. 48, pp. 3384–3395, 1983.

Charles E. Boozer et al, "Air Oxidation of Hydrocarbons.[1] II. The Stiochiometry and fate of Inhibitors in Benzene and Chlorobenzene", Journ. Amer. Chem. Soc., vol. 77, pp. 3233–3237, Jun. 20, 1955.

F. Feichtmayr et al, "Dipolmomente Und Struktur Von Carbodiimiden", Berichte der Bunsengesellschaft, vol. 67, pp. 434–438, 1963.

Jean Piccard, "Ueber Farben Zweiter Ordnung und Ueber Hold– Und Meri–Chinoide Salze", Chem. Ber., vol. 46, pp. 1843–1860, 1913.

E.V. Bandrowsky, Montash. Chemie, vol. 8, p. 478 (with English Translation of p. 478), 1887.

*Primary Examiner*—Paul F. Shaver
*Attorney, Agent, or Firm*—Oblon, Spivak, McClelland, Maier & Neustadt, P.C.

[57] ABSTRACT

The invention relates to a process for preparing N,N'-disubstituted p-quinonediimines of general formula I

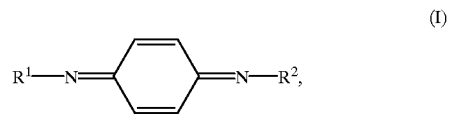

(I)

wherein a corresponding N,N'-disubstituted p-phenylenediamine is oxidized in alkaline/alcoholic solution, and also their use. The invention further provides organosilanes containing methacryloxy or acryloxy groups and having general formula II

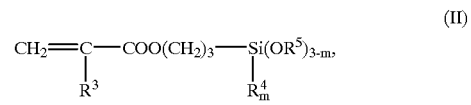

(II)

where $R^3$ is a hydrogen atom or a methyl group and $R^4$ and $R^5$ are identical or different alkyl groups having from 1 to 4 carbon atoms and m is equal to 0 or 1 or 2, which organosilanes contain N,N'-disubstituted p-quinonediimines. Processes for preparing and stabilizing organosilanes of general formula II are described.

9 Claims, No Drawings

PROCESS FOR PREPARING N, N'-DISUBSTITUTED P-QUINONEDIIMINES, THEIR USE AND ORGANOSILANES CONTAINING METHACRYLOXY OR ACRYLOXY GROUPS, PROCESSES FOR THEIR STABILIZATION AND THEIR PREPARATION

This appln is a Div of Ser. No. 08/543,932 filed Oct. 17, 1995, U.S. Pat. No. 5,856,542.

BACKGROUND OF THE INVENTION

1. Field of the Invention

The invention relates to a process for preparing N,N'-disubstituted p-quinonediimines of general formula I

(I)

where $R^1$ and $R^2$ are identical or different and are each a phenyl group and/or a straight-chain and/or branched alkyl group having from 3 to 8 carbon atoms and/or a cyclohexyl group, and also their use. The invention further relates to organosilanes containing methacryloxy or acryloxy groups and having general formula II

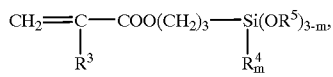
(II)

where $R^3$ is a hydrogen atom or a methyl group, $R^4$ and $R^5$ are identical or different alkyl groups having from 1 to 4 carbon atoms, m is equal to 0, 1 or 2, a process for their preparation and a process for their stabilization. The organosilanes of general formula II are hereinafter also referred to as acrylsilanes.

2. Discussion of the Background

N,N'-disubstituted p-quinonediimines of general formula I are not commercial products, but nevertheless are compounds having interesting chemical and physical properties.

In the known processes for preparing N,N'-disubstituted p-quinonediimines, hereinafter also referred to as simply diimines, the starting materials used are the corresponding N,N'-disubstituted p-phenylenediamines which are converted into the corresponding diimines by the action of oxidizing agents. Hereinafter, the N,N'-disubstituted p-phenylenediamines are also referred to simply as diamines. The processes for preparing the diimines gives, according to the prior art, either only low yields or impure products, are uneconomical, or extremely toxic compounds are used.

Thus, the preparation of N,N'-diphenyl-p-quinonediimine from the corresponding diamine by oxidation with chromic acid in dilute acetic acid solution has been described (Chem. Ber. 46 (1913) p. 1853). The diimine formed is obtained in an amorphous form which is difficult to purify and has to be purified by repeated recrystallization. As byproducts, there are formed relatively large amounts of a chromium-containing, aqueous, acetic acid solution which can be disposed of only with difficulty.

It is further known that N,N'-diphenyl-p-quinonediimine can be prepared by shaking a benzene solution of N,N'-diphenyl-p-phenylenediamine with an aqueous potassium ferricyanide solution (P. Feichtmayr and F. Würstlin, Berichte der Bunsengesellschaft Vol. 67 (1963) p. 435). Since the reactants are present in separate phases, the reaction proceeds very slowly and the yields are unsatisfactory.

The same process is also described for the preparation of N-phenyl-N'-isopropyl-p-quinonediimine and N-phenyl-N'cyclohexyl-p-quinonediimine (L. Kotulak et al., Collect. Czech. Chem. Commun. 48 (1983) 12, p. 3384–3395).

The use of silver oxide in place of potassium ferricyanide as an oxidizing agent has also been proposed (L. Kotulak et al., Collect. Czech. Chem. Commun. 48 (1983) 12, p. 3384–3395). However, silver oxide is a very expensive and difficult-to-handle chemical.

The preparation of N,N'-disubstituted p-quinonediimines by air oxidation of the corresponding diamines is also known. Thus, N,N'-diphenyl-p-phenylenediamine is converted into a diimine by atmospheric oxygen in the presence of high excesses of azobisisobutyronitrile (AIBN) (C. E. Boozer et al., Journ. Amer. Chem. Soc., 77 (1955) p. 3233). Disadvantages of this process are the toxicity of the AIBN used, the use of chlorobenzene as solvent and the low yields.

U.S. Pat. No. 2,118,826 describes the oxidation of N,N'-disubstituted p-arylenediamines to the corresponding p-quinonediimines using air in the presence of solid alkali metal or alkali earth metal oxides, hydroxides, carbonates or amides. Disadvantages are the solid-state reaction, the high reaction temperatures of from 130 to 180° C. and also long reaction times of up to 8 hours, with considerable decomposition of the diimines formed taking place.

Although the additional use of heavy metal salts as catalysts can lower the reaction temperatures, these salts can be removed only with difficulty from the N,N'-disubstituted p-quinonediimines obtained.

EP-B 0 437 653 teaches the synthesis of organosilanes of general formula II by reacting alkali metal salts of methacrylic acid or acrylic acid with chloropropylsilanes of general formula III,

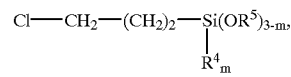
(III)

where $R^4$, $R^5$ and m are as defined above, in the presence of phase-transfer catalysts of the tetraalkylammonium type, with N,N'-diphenyl-p-phenylenediamine being used as stabilizer in the examples presented to prevent undesired polymer formation, in particular the formation of "popcorn" polymer. It is known that, for example, heavy metal salts can trigger the undesired polymerization of the acrylsilanes and also can accelerate the siloxane formation of alkoxysilane functions. The purification of the acrylsilanes is carried out by distillation.

The synthesis of the acrylsilanes by the phase-transfer catalysis process, hereinafter also referred to as PTC process, generally comprises four individual steps:

Stage 1: Preparation of the alkali metal methacrylate or acrylate

Stage 2: Reaction of these salts with chloropropylalkoxysilanes in the presence of the phase-transfer catalyst to give the acrylsilane Stage 3: Separation of the accompanying product alkali metal chloride Stage 4: Distillative workup of the crude product The addition of the stabilizer system is generally carried out after the first process stage, the preparation of the alkali metal acrylates.

Not very advantageous in the PTC process is the fact that the above-mentioned stabilizer does not go into the vapor phase in the fourth stage, the distillative workup of the crude organosilanes of general formula II, owing to its low volatility. This can lead, in particular for continuous process operation, to the formation of "popcorn" polymer in the distillation columns or the pipe systems, resulting in operating faults or even to damage of the plant.

DE-C 38 32 621 discloses, for improving the stabilization of acrylsilanes prepared by the process of addition of trialkylsilanes to allyl methacrylate using $H_2PtCl_6$ as catalyst, stabilizer combinations of N,N'-disubstituted p-phenylenediamines and sterically hindered phenols, with, in the distillate workup of the crude acrylsilanes, the diamines taking over the stabilization of the liquid phase and the volatile phenols taking over the stabilization of the vapor phase. The industrial implementation of this process provides for the addition of the stabilizers prior to or after completion of the synthesis steps. However, the achievable yields of acrylsilanes are unsatisfactory.

In addition, the stabilizer combination of N,N'-disubstituted diamines and sterically hindered phenols proves to ineffective when the acrylsilane synthesis is carried out by the PTC process. Here, addition of the stabilizer combination in the course of or after completion of the first process stage, the preparation of the alkali metal methacrylate or acrylate from alcoholic alkali metal alkoxide solution and methacrylic acid or acrylic acid customary in the process, results in the phenolic component being converted into non-volatile alkali metal phenoxide, indeed independently of whether the acid or the alkoxide is initially charged in the preparation of the salt. In the distillative workup of the crude acrylsilanes, the free, volatile phenol is thus not available, causing "popcorn" polymer formation in the columns and giving a poorer product yield.

SUMMARY OF THE INVENTION

It is, therefore, an object of the invention to provide an economical and environmentally compatible process for preparing N,N'-disubstituted p-quinonediimines, and also to provide a stabilizer system which prevents polymerization of the organosilanes of general formula II during the preparative process, particularly also in the distillative product workup.

It has now surprisingly been found that the formation of a p-quinonediimine from the corresponding N,N'-disubstituted diamine takes place particularly well in an alkaline/alcoholic solution in the presence of suitable oxidizing agents. A corresponding diamine is an N,N'-disubstituted p-phenylenediamine of general formula IV

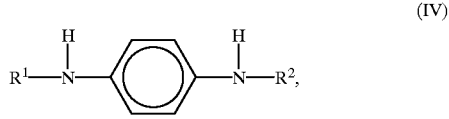

where $R^1$ and $R^2$ are the same organic radicals as those in the N,N'-disubstituted p-quinonediimines of general formula I. A suitable oxidizing agent has been found to be, for example, molecular oxygen. In contrast, the oxidation does not take place or takes place only to an insufficient extent in acid or neutral medium. It has further been found that particularly suitable alkaline/alcoholic media in the oxidation of the diamines are alkali metal alkoxide solutions; but it is also possible to use alkali metal hydroxide solutions, appropriately those based on alcohols.

It has also been found that N,N'-disubstituted p-quinonediimines of general formula I effect stabilization of the acrylsilanes during their preparation, in particular in their distillative workup, both in the liquid phase and in the vapor phase, and also lead to improved yields.

It was particularly surprising that N,N'-disubstituted p-quinonediimines can also be generated during the PTC preparation process by targeted oxidation of N,N'-disubstituted p-phenylenediamines of general formula IV, without otherwise adversely affecting the course of the process and the synthesis of the acrylsilanes. Thus, the PTC process was able to be significantly further improved in a simple and economical manner.

DETAILED DESCRIPTION OF THE PREFERRED EMBODIMENTS

The present invention accordingly provides a process for preparing N,N'-disubstituted p-quinonediimines of general formula I

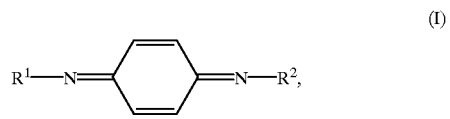

where $R^1$ and $R^2$ are identical or different and are each a phenyl group and/or a straight-chain and/or branched alkyl group having from 3 to 8 carbon atoms and/or a cyclohexyl group, in which the corresponding N,N'-disubstituted p-phenylenediamines are oxidized in alkaline/alcoholic solution.

The invention additionally provides for the use of N,N'-disubstituted p-quinonediimines of general formula I, where $R^1$ and $R^2$ are identical or different and are each a phenyl group and/or a straight-chain and/or branched alkyl group having from 3 to 8 carbon atoms and/or a cyclohexyl group, for stabilizing organosilanes containing methacryloxy or acryloxy groups and having general formula II

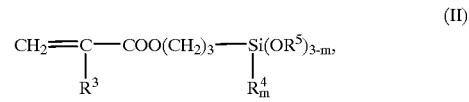

where $R^3$ is a hydrogen atom or a methyl group, $R^4$ and $R^5$ are identical or different alkyl groups having from 1 to 4 carbon atoms and m is equal to 0, 1 or 2.

The invention further provides organosilanes containing methacryloxy or acryloxy groups and having general formula II

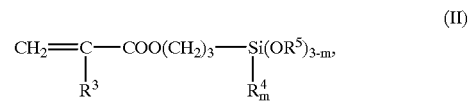

where $R^3$ is a hydrogen atom or a methyl group, $R^4$ and $R^5$ are identical or different alkyl groups having from 1 to 4 carbon atoms, and m is equal to 0, 1 or 2, which contain as stabilizers one or more N,N'-disubstituted p-quinonediimines of general formula I

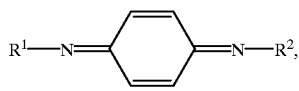

where $R^1$ and $R^2$ are identical or different and are each a phenyl group and/or a straight-chain and/or branched alkyl group having from 3 to 8 carbon atoms and/or a cyclohexyl group.

The present invention further provides a process for stabilizing organosilanes containing methacryloxy or acryloxy groups and having general formula II

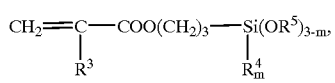

where $R^3$ is a hydrogen atom or a methyl group, $R^4$ and $R^5$ are identical or different alkyl groups having from 1 to 4 carbon atoms, and m is equal to 0, 1 or 2, in which N,N'-disubstituted p-quinonediimines of general formula I

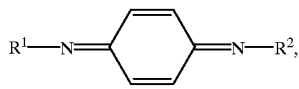

where $R^1$ and $R^2$ are identical or different and are each a phenyl group and/or a straight-chain and/or branched alkyl group having from 3 to 8 carbon atoms and/or a cyclohexyl group, are used as stabilizers.

The invention also provides a phase-transfer catalysis process (PTC process) for preparing organosilanes containing methacryloxy or acryloxy groups and having general formula II

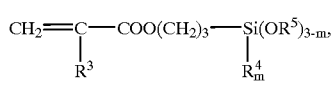

where $R^3$ is a hydrogen atom or a methyl group, $R^4$ and $R^5$ are identical or different alkyl groups having from 1 to 4 carbon atoms, and m is equal to 0, 1 or 2, in which crude organosilanes of general formula II are stabilized during the PTC process by N,N'-disubstituted p-quinonediimines of general formula I

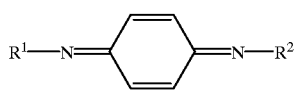

where $R^1$ and $R^2$ are identical or different and are each a phenyl group and/or a straight-chain and/or branched alkyl group having from 3 to 8 carbon atoms and/or a cyclohexyl group.

In the process of the invention for preparing p-quinonediimines of general formula I, the alkaline component of the alkaline/alcoholic solution used in the oxidation of the corresponding diamines can be an alkali metal alkoxide and/or an alkali metal hydroxide. Suitable alkoxides include alkoxides having 1–8 carbon atoms, preferably 1–4 carbon atoms.

The alkaline/alcoholic solution preferably contains from 5 to 15% by weight of alkali metal alkoxides. However, higher or lower alkoxide concentrations can also be used. At concentrations higher than 15% by weight there is increasing formation of N,N'-disubstituted 2,5-dialkoxy-p-quinonediimines as byproducts and at concentrations lower than 5% by weight the oxidation proceeds increasingly slowly. Preferred alkali metal alkoxides are the methoxides and ethoxides of sodium and potassium.

Alcohols which can be used here are, for example, primary, secondary or tertiary alcohols having from 1 to 6 carbon atoms in the carbon skeleton, with preference being given to methanol and ethanol.

For the oxidation, the diamine of general formula IV can be present completely or else only partially dissolved in the alkoxide solution used.

Preference is given to a rapid oxidation to keep the formation of byproducts low. The oxidation is preferably carried out at a temperature between 10 and 60° C., particularly preferably at a temperature between 20 and 40° C., very particularly preferably at a temperature between 25 and 35° C.

The oxidizing agent used can be molecular oxygen. Preferably, the oxidizing agent used is oxygen in admixture with nitrogen. When the oxidizing agent is an oxygen-nitrogen mixture, it preferably contains more than 0.1 and less than 21% by volume of oxygen, particularly preferably more than 0.1 and less than 8.4% by volume of oxygen. The reaction is preferably carried out at atmospheric pressure, but it can also be carried out at higher pressures, appropriately up to 5 bar.

The diimines prepared or used according to the invention can also be present in impure form, the product of the oxidation reaction being able to contain a mixture of N,N'-disubstituted p-phenylenediamine and N,N'-disubstituted p-quinonediimine. Even at a 10% conversion of the diamine to the diimine, the addition to organosilanes of general formula II has a stabilizing effect, but the diamine conversion is preferably more than 30%.

The diimines preferred according to the invention can be prepared in pure form by customary workup methods such as, for example, distillative work-up under reduced pressure, recrystallization or column chromatography. However, use in analytically pure form is not a precondition for the use according to the invention of the diimines.

For the organosilanes of the invention of general formula II, the content of p-quinonediimines of general formula I is preferably greater than 0.0005 to 1.5% by weight, particularly preferably from 0.01 to 1.0% by weight, very particularly preferably from 0.1 to 0.5% by weight.

As additional stabilizers, the organosilanes of the invention can contain N,N'-disubstituted p-phenylenediamines of general formula IV

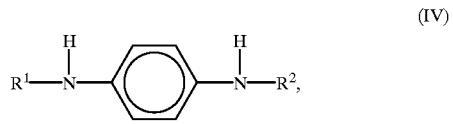

where $R^1$ and $R^2$ are identical or different and are each a phenyl group and/or a straight-chain and/or branched alkyl group having from 3 to 8 carbon atoms and/or a cyclohexyl group, and/or volatile, sterically hindered phenols of general formula V

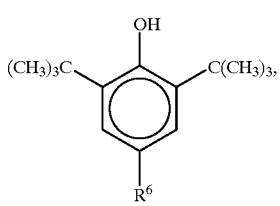

where $R^6$ is an alkyl or alkoxy group having from 1 to 4 carbon atoms.

In the PTC process described above, organosilanes of general formula II are obtained from alkali metal methacrylates or alkali metal acrylates and chloropropylalkoxysilanes of general formula III

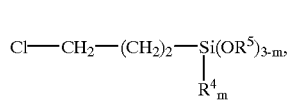

where $R^4$ and $R^5$ are identical or different alkyl groups having from 1 to 4 carbon atoms and m is 0 or 1 or 2.

According to the process of the invention for stabilizing organosilanes containing methacryloxy or acryloxy groups and having general formula II, the p-quinonediimines of general formula I used as stabilizers can be added during the preparation process of the organosilanes of general formula II.

The p-quinonediimines of general formula I used as stabilizers can, however, also be generated during the preparation process of the organosilanes of general formula II. Here, the p-quinonediimines of general formula I can be produced by oxidation of the corresponding p-phenylenediamines of general formula IV, in the presence of an oxidizing agent. The oxidizing agent used is preferably oxygen in admixture with nitrogen. The oxidation is preferably carried out at a temperature between 10 and 60° C., particularly preferably at a temperature between 20 and 40° C., very particularly preferably at a temperature between 25 and 35° C.

The p-quinonediimines of general formula I can thus be produced, for example, by oxidation of the corresponding p-phenylenediamines of general formula IV in the reaction medium of stage 1 of the PTC process.

The procedure can be that the initially charged amount of alkali metal alkoxide is first neutralized by addition of methacrylic acid or acrylic acid to such an extent that in a, for example, methanolic solution, the proportion by weight of the dissolved alkali metal alkoxide remaining after subtraction of the resulting amount of salt is between 5 and 15% by weight.

After introduction of an N,N'-disubstituted diamine of general formula IV, the desired conversion of the diamine into the diimine can be brought about by the targeted $O_2$ oxidation. The molecular oxygen used as oxidizing agent can be diluted by an inert gas, preferably nitrogen, to such an extent that explosive mixtures are not formed with the components present in the above-mentioned system.

Subsequently, further acid can be added for stoichiometric salt formation. However, a small excess of alkoxide can also remain, so that a homogenized alcoholic salt sample mixed with water in a ratio of 1:1 has a pH between 8 and 11.

In this alkaline/alcoholic medium, the diimines prepared according to the invention are found to be stable even over a prolonged period of time.

After carrying out the phase-transfer catalyzed reaction in stage 2 or after the salt separation in stage 3, the crude organosilane of general formula II is obtained. The crude organosilanes of general formula II, here stabilized according to the invention, preferably contain from greater than 0.0005 to 1.5% by weight, particularly preferably from 0.01 to 1.0% by weight, very particularly preferably from 0.1 to 0.5% by weight, of p-quinonediimines of general formula I. Preferred N,N'-disubstituted p-quinonediimines are those which have a volatility which is not higher than the boiling point of the acrylsilane to be stabilized. Preferably, the volatilities of the diimines are only insignificantly below the boiling points of the acrylsilanes.

As is shown in practice, the p-quinonediimines of general formula I used as stabilizers can be added and/or generated during the PTC process.

However, in the process of the invention for stabilizing the organosilanes of general formula II, it is also possible to use, as additional stabilizers, N,N'-disubstituted p-phenylenediamines of general formula IV

where $R^1$ and $R^2$ are identical or different and are a phenyl group and/or a straight-chain and/or branched alkyl group having from 3 to 8 carbon atoms and/or a cyclohexyl group, and/or volatile, sterically hindered phenols of general formula V

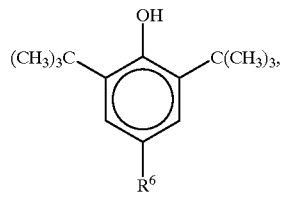

where $R^6$ is an alkyl or alkoxy group having from 1 to 4 carbon atoms. The phenolic stabilizers appropriately have boiling points comparable to those of the acrylsilanes of general formula II.

The purification of the organosilanes of general formula II is usually carried out by distillation. This can be carried out using short-path or thin-film evaporators and/or by column distillation.

The crude organosilanes of general formula II containing p-quinonediimines of general formula I are preferably subjected to flash distillation to remove high boiling components. For the purposes of the present invention, flash distillation is a distillative pre-purification, for example via a thin-film evaporator.

A preferred embodiment of the distillative workup of the crude products of the acrylsilanes comprises the combination of flash distillation (preliminary stage) and column distillation. In the preliminary stage, catalysts, unreacted diamines, residual salts and small amounts of polymer can be removed.

The flash distillate is stabilized using an amount, preferably from greater than 5 to 15000 ppm by weight, particularly preferably from 10 to 3000 ppm by weight and very particularly preferably from 50 to 1000 ppm by weight, of the p-quinonediimines of general formula I. The flash distillate is subsequently fractionally distilled in an appropriate manner.

An advantage of the diimines prepared and used according to the invention is that they have a high volatility and, in the distillation of the acrylsilanes, also get into the vapor phase and there also have a stabilizing, i.e. polymerization-preventing, effect. The organosilanes containing methacryloxy or acryloxy groups, which are distilled over via the top of the column, are preferably obtained free of p-quinonediimines of general formula I.

After the fractional distillation, a non-coloring, sterically hindered phenol of general formula V is preferably added to the organosilanes containing methacryloxy or acryloxy groups and having general formula II for post-stabilization; preference is given to adding 2,6-di-tert-butyl-4-methylphenol. The distillative workup can be carried out either batchwise or continuously.

The concentration of the N,N'-disubstituted diimines is appropriately determined photometrically.

In the PTC process of the invention, the p-quinonediimines of general formula I and N,N'-disubstituted p-phenylenediamines of general formula IV

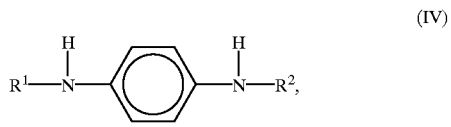

(IV)

where $R^1$ and $R^2$ are identical or different and are each a phenyl group and/or a straight-chain and/or branched alkyl group having from 3 to 8 carbon atoms and/or a cyclohexyl group, can be added to the starting material mixture and/or the reaction mixture and/or the crude organosilane of general formula II and/or the flash distillate and/or at another point in the distillative workup and/or the said organosilane obtained by said fractionally distilling step. Furthermore, volatile, sterically hindered phenols of general formula V

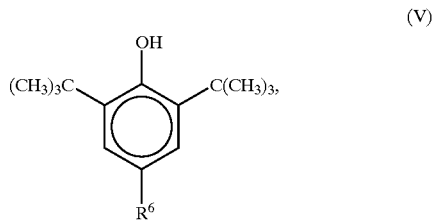

(V)

where $R^6$ is an alkyl or alkoxy group having from 1 to 4 carbon atoms, can be added to the crude organosilane of general formula II and/or the flash distillate and/or at an another point in the distillative workup and/or to the pure distillate.

All distillations are appropriately carried out under reduced pressure; the preferred working pressures are between 0.01 and 50 mbar.

Suitable N,N'-disubstituted diimines are, for example:
N,N'-diphenyl-p-quinonediimine,
N,N'-di(1-methylheptyl)-p-quinonediimine,
N,N'-di(1-ethyl-3-methylpentyl) -p-quinonediimine,
N,N'-di(1,4-dimethylpentyl)-p-quinonediimine,
N,N'-di-sec-butyl-p-quinonediimine,
N-phenyl-N'-cyclohexyl-p-quinonediimine, and
N-phenyl-N'-isopropyl-p-quinonediimine.

Suitable N,N'-disubstituted diamines are, for example:
N,N'-diphenyl-p-phenylenediamine,
N,N'-dinaphthyl-p-phenylenediamine,
N,N'-di(1-methylheptyl)-p-phenylenediamine,
N,N'di(1-ethyl-3-methylpentyl)-p-phenylenediamine,
N,N'-di(1,4-dimethylpentyl)-p-phenylenediamine,
N,N'-di-sec-butyl-p-phenylenediamine,
N-phenyl-N'-cyclohexyl-p-phenylenediamine, and
N-phenyl-N'-isopropyl-p-phenylenediamine.

Suitable, sterically hindered phenols are, for example:
2,6-di-tert-butyl-4-methylphenol,
2,6-di-tert-butyl-4-ethylphenol,
2,6-di-tert-butyl-4-methoxyphenol.

The process of the invention for preparing N,N'-disubstituted p-quinonediimines makes it possible, in the preparation of methacryloxy- or acryloxy-containing organosilanes of general formula II, in particular in the PTC process, in a simple manner to prevent "popcorn" polymerization and to obtain acrylsilanes of high purity and colorless appearance. Particularly, organosilanes of general formula II used for the preparation of polymers have to meet high quality requirements.

A further substantial advantage of the measures of the invention is that the yield of in-specification acrylsilanes and thus the economics of the PCT process was able to be further improved.

The invention is illustrated by the following examples.

EXAMPLES

Example 1

Preparation of N,N'-diphenyl-p-quinonediimine:

57 g of technical-grade N,N'-diphenyl-p-phenylenediamine (commercial product PERMANAX DPPD® from Akzo) having a melting range from 134 to 140° C. was distilled under nitrogen at 0.1 mbar. The fraction going over at from 196 to 200° C. was collected. Yield: 44.5 g, about 78.1% of theory; melting point: 135–138° C. 33 g of distillate were recrystallized from acetone/methanol. Yield: 82.0% of theory; melting point: 149–150° C.

A lively gas stream of $O_2$ and $N_2$ (1:11) was passed at a temperature of about 30° C. into a solution of 22 g of N,N'-diphenyl-p-phenylenediamine in 5 liters of 8% strength potassium methoxide/methanol solution while stirring. After 3 hours, the N,N'-diphenyl-p-quinonediimine yield was 78%. The yield was determined photometrically from the absorbance at the absorption maximum of 442 nm. The precipitated solid was filtered off. The melting point was determined after recrystallization from acetone/methanol: 181–183° C.

Example 2

926.1 g of a 25.4% strength potassium methoxide solution were admixed while stirring and cooling with 289.0 g of methacrylic acid. 4.2 g of the N,N'-diphenyl-p-quinonediimine prepared according to Example 1, 15.2 g of tetrabutylammonium bromide and 680.3 g of 3-chloropropyltrimethoxysilane were added and methanol was distilled off via a short column, if desired with application of vacuum, until an exothermic reaction commenced at 115° C. After this had abated, heating was continued for 2 hours at 120° C. The precipitated potassium chloride was filtered off from the cooled mixture and washed with methanol. The filtrate free of methanol was flash distilled at 0.4 mbar via a Claisen bridge: boiling point 88–90° C. Amount of distillate: 766.8 g, about 92.1% of theory. The yellow-orange distillate contained, according to photometric determination, 80 mg of N,N'-diphenyl-p-quinonediimine/kg.

Fractional distillation via a packed column equipped with Raschig rings gave 722.3 g, about 86.7% of theory, of 3-methacryloxypropyltrimethoxysilane. Boiling point: 81–82° C./0.2 mbar; GC purity: 99.7%.

Prior to commencement of the pure distillation, 144 mg of 2,6-di-tert-butyl-4-methylphenol (commercial product IONOL CP from Shell) were introduced into the distillation receiver. During the flash and pure distillation, small amounts of an $O_2/N_2$ mixture having an $O_2:N_2$ ratio of 1:11.5 were bubbled into the column bottoms.

After the distillations, no evidence of "popcorn" polymers was to be found in the apparatus used, in the distillates or bottoms.

Example 3

In a stirred reactor, 13.613 kg of a methanolic 25.7% strength potassium methoxide solution were admixed while cooling with 2.868 kg of anhydrous methacrylic acid and, after addition of 62.5 g of N,N'-diphenyl-p-phenylenediamine, a lively gas stream comprising an oxygen-nitrogen volume mixture of 1:12 was passed in at from about 20 to 30° C. until the photometrically determinable diamine conversion to N,N'-diphenyl-p-quinonediimine was 55%. After addition of a further 1.432 kg of methacrylic acid, sufficient further potassium methoxide solution was added for a homogenized methanol/salt sample to have, after dilution with water in a ratio of 1:1, a pH of 9.5. After addition of 225.8 g of tetrabutylammonium bromide and 10.0 kg of 3-chloropropyltrimethoxysilane, methanol was distilled off via a short column until an exothermic reaction commenced at 118° C., which reaction was kept at a temperature of below 120° C. by cooling. After the exothermic reaction had abated, heating was continued for 2 hours at 120° C. The potassium chloride formed was centrifuged from the cooled reaction mixture and washed with methanol. The diimine content of the methanol-free filtrate was determined photometrically as 2.8 g/kg. After distillation via a short-path evaporator (model KD 10 from Leybold-Heraeus) under an oxygen/nitrogen stream (volume ratio 1:12) of 1750 ml/h, at an evaporator temperature of 94° C. and a working pressure of 0.4 mbar, a distillation yield of 11.557 kg, about 93.2% was achieved. The diimine content determined photometrically was 92 mg/kg of distillate.

After addition of 3.467 g of 2,6-di-tert-butyl-4-methylphenyl, fractionation was carried out via a 40 cm column (column packing $V_4A$ wire mesh) under an $O_2/N_2$ stream (volume ratio 1:11.9) of 150 liter/h. Yield: 11.146 kg, about 90.0% of theory, of 3-methacryloxypropyltrimethoxysilane. Boiling point: 76–77° C./0.25 mbar. GC purity: 99.6%.

Popcorn polymer was found neither in the distillation residues nor in the short-path evaporator or distillation column.

Example 4

In a stirred reactor, 9.807 kg of a 25.7% strength methanolic potassium methoxide solution was admixed while cooling with 1.711 kg of acrylic acid and, after addition of 45 g of pulverulent N,N'-diphenyl-p-phenylenediamine, a lively gas stream comprising an oxygen/nitrogen mixture (1:11.5) was passed through the reaction mixture for 2 hours at from about 30 to 40° C. After this time, the diamine conversion determined photometrically was 63%. After addition of a further 0.882 kg of acrylic acid and taking of a sample, the latter had, after dilution with water in a ratio of 1:1, a pH of 8.5.

After addition of 163 g of tetrabutylammonium bromide and 7.190 kg of 3-chloropropyltrimethoxysilane, methanol was distilled off via a short column until an exothermic reaction commenced at 115° C. After this had abated, heating was continued for 1.5 hours at 120° C. After cooling, the solution was centrifuged off from the potassium chloride formed and the latter was washed with methanol. The diimine content in the filtrate free of methanol was determined photometrically as 3.2 g/kg of filtrate.

After distillation via a short-path evaporator (model KD 10 from Leybold-Heraeus), at an evaporator temperature of 95° C. and a working pressure of 0.4 mbar with passing in of an oxygen/nitrogen mixture (volume ratio 1:15) at 1050 ml/h, a distillation yield of 94.3% of theory was achieved. The diimine content determined photometrically was 80 mg/kg of distillate.

After addition of 1.9 g of 2,6-di-tert-butyl-4-methylphenol, fractionation was carried out via a 40 cm packed column under the above-mentioned oxygen/nitrogen ratio and with a gas inflow of 100 ml/h. Pure yield: 7.991 kg, about 89.5% of theory, of 3-acryloxypropyltrimethoxysilane. Boiling point: 63–64° C./0.1–0.15 mbar. GC purity: 99.3%.

Popcorn polymer was present neither in the distillation residues nor in the short-path evaporator or distillation column.

Example 5

255 g of allyl methacrylate and 3 g of 2,6-di-tert-butyl-4-methylphenol were placed in a multineck flask fitted with stirrer, dropping funnel, thermometer and condenser and were heated to 105° C. while passing in a slow stream of oxygen/nitrogen (volume ratio 1:11.9). 240 g of trimethoxysilane were added dropwise from the dropping funnel. After addition of a quarter, half and three quarters of the silane, and also after completion of the silane addition, 250 mg of a 10% strength acetone solution of $H_2PtCl_6$ were added in each case. During the reaction, the temperature was kept between 100 and 105° C. After a reaction time of 2 hours, the crude product obtained was flash distilled in vacuo.

After addition of 4.5 g of N-phenyl-N'-isopropyl-p-quinonediimine, the residue was distilled under reduced pressure via a short packed column, with 417.6 g of 3-methacryloxypropyltrimethoxysilane going over as main fraction at from 110 to 112° C., which corresponds to a yield of 85.6%, based on allyl methacrylate used.

No popcorn polymer was present in the column, the distillation residue was non-viscous, and the distillate had a Hazen number of less than 10.

Comparative Example A

The procedure differed from Example 2 in that, in place of N,N'-diphenyl-p-quinonediimine, 4.2 g of N,N'-diphenyl-p-phenylenediamine were used with substantial exclusion of oxygen. The flash distillate was virtually colorless and contained less than 5 mg of diimine per kg of distillate. In the pure distillation via a column without use of an oxygen-containing protective gas, a considerable amount of popcorn polymer formation occurred in the column and in the bottoms. The yield was 42%.

Comparative Example B

The procedure of Example 2 was altered in that, in place of N,N'-diphenyl-p-quinonediimine, 4.2 g of N,N'-diphenyl-p-phenylenediamine and 0.23 g of 2,6-di-tert-butyl-4-methylphenol were added immediately after the formation of potassium methacrylate. The reaction was carried out with substantial exclusion of oxygen.

The flash distillate was virtually colorless and contained less than 5 mg of diimine per kg of distillate. The GC analysis gave no sign of 2,6-di-tert-butyl-4-methylphenol in the flash distillate.

In the pure distillation via a column, without use of an oxygen-containing protective gas, a substantial amount of popcorn polymer formation occurred in the column and in the bottoms. The yield was 39%.

Obviously numerous modifications and variations of the present invention are possible in light of the above teachings. It is, therefore, to be understood that within the scope of the appended claims, the invention may be practiced otherwise than as specifically described therein.

What is claimed as new and desired to be secured by Letters Patent of the U.S. is:

1. A process for preparing N,N'-disubstituted p-quinonediimines of formula I

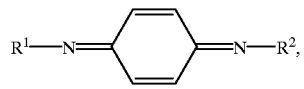

(I)

wherein $R^1$ and $R^2$ are identical or different and are each a phenyl group, a straight-chain or branched alkyl group having from 3 to 8 carbon atoms, or a cyclohexyl group, comprising oxidizing a N,N'-disubstituted p-phenylenediamine of the formula

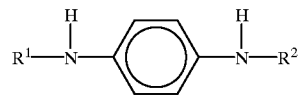

wherein $R^1$ and $R^2$ are as described above, in an alkaline/alcoholic solution in the presence of an oxidizing agent at a temperature between 10 and 60° C.

2. The process of claim 1, wherein said oxidizing agent used is molecular oxygen.

3. The process of claim 2, wherein said oxidizing agent is a mixture of molecular oxygen and nitrogen.

4. The process of claim 3, wherein said molecular oxygen/nitrogen mixture contains more than 0.1 and less than 21% by volume of molecular oxygen.

5. The process of claim 4, wherein said molecular oxygen/nitrogen mixture contains more than 0.1 and less than 8.4% by volume of molecular oxygen.

6. The process of claim 1, wherein said alkaline/alcoholic solution comprises an alkali metal alkoxide, alkali metal hydroxide or mixture thereof.

7. The process of claim 6, wherein said alkaline/alcoholic solution contains from 5 to 15% by weight of alkali metal alkoxide.

8. The process of claim 1, wherein said oxidizing is carried out at a temperature between 20 and 40° C.

9. The process of claim 1, wherein said oxidizing is carried out at a temperature between 25 and 35° C.

* * * * *